(12) United States Patent
Wijesekera et al.

(10) Patent No.: US 6,169,202 B1
(45) Date of Patent: Jan. 2, 2001

(54) WELLS-DAWSON TYPE HETEROPOLYACIDS, THEIR PREPARATION AND USE AS OXIDATION CATALYSTS

(75) Inventors: Tilak P. Wijesekera, Glen Mills; James E. Lyons, Wallingford; Paul E. Ellis, Jr., Malvern, all of PA (US)

(73) Assignees: Sunoco, Inc. (R&M); Rohm and Haas Company, both of Philadelphia, PA (US)

(*) Notice: Under 35 U.S.C. 154(b), the term of this patent shall be extended for 0 days.

(21) Appl. No.: 09/524,157

(22) Filed: Mar. 14, 2000

Related U.S. Application Data

(60) Division of application No. 09/135,409, filed on Aug. 14, 1998, now Pat. No. 6,060,419, which is a continuation-in-part of application No. 09/002,816, filed on Jan. 5, 1998, now Pat. No. 6,043,184, which is a continuation-in-part of application No. 09/002,845, filed on Jan. 5, 1998, now Pat. No. 5,990,348.

(51) Int. Cl.[7] ............................ C07C 51/16; C07C 27/10; C07C 53/00

(52) U.S. Cl. ........................................ 562/549; 562/512.2

(58) Field of Search ..................... 562/512.2, 549

(56) References Cited

U.S. PATENT DOCUMENTS

| | | | |
|---|---|---|---|
| 4,196,136 | 4/1980 | Knoth, Jr. | 556/10 |
| 4,630,176 | 12/1986 | Cuellar et al. | 361/502 |
| 4,634,502 | 1/1987 | Callahan et al. | 205/148 |
| 4,803,187 | 2/1989 | Lyons et al. | 502/200 |
| 4,859,798 | 8/1989 | Lyons et al. | 568/399 |
| 4,898,989 | 2/1990 | Ellis, Jr. et al. | 568/399 |
| 4,916,101 | 4/1990 | Lyons et al. | 502/209 |
| 5,079,203 | 1/1992 | Pinnavaia et al. | 502/84 |
| 5,091,354 | 2/1992 | Ellis, Jr. et al. | 502/200 |
| 5,191,116 | 3/1993 | Yamamatsu et al. | 562/549 |
| 5,334,780 | 8/1994 | Shaikh et al. | 568/910 |
| 5,377,039 | 12/1994 | Babinec | 359/265 |
| 5,385,876 | 1/1995 | Schwartz et al. | 502/80 |
| 5,616,815 | 4/1997 | Atkins | 568/700 |
| 5,629,459 | 5/1997 | Atkins | 568/896 |
| 5,684,216 | 11/1997 | Haining | 568/896 |
| 5,705,685 | 1/1998 | Lyons et al. | 562/549 |
| 5,714,429 | 2/1998 | Haining | 502/232 |

FOREIGN PATENT DOCUMENTS

| | | |
|---|---|---|
| 0 418 657 A2 | 3/1991 | (EP) . |
| 0 425 666 B1 | 4/1994 | (EP) . |
| 2-42033 | 2/1990 | (JP) . |
| 6-218286 | 8/1994 | (JP) . |

OTHER PUBLICATIONS

M. Ai, "Partial Oxidation of n-Butane with Heteropoly, Compound-based Catalysts." Labo. Resources Utiliz. Tokyo Inst. Tech., Yokohama, Japan *Proceedings of the 18th International Congress on Catalysts, vol. V: Cluster-derived catalysts, Active phase support interactions, Catalysts for synthesis of Chemicals*, Verlag Chemie, vol. 5, p. V475–V486, Berlin, (1984) Month N/A.

M. Ai, "Oxidation of Propane to Acrylic Acid." *Catalysis Today*, vol. 13 (4), pp. 679–684 (Eng.) (1992).

Blake, et al., "Magnetic and Spectroscopic Properties of Some Heterotrinuclear Basic Acetates of Chromium (III), Iron (III), and Divalent Metal Ions." *J. Chem. Soc. Dalton Trans.*, pp. 2509–2520, Feb. (1985).

(List continued on next page.)

*Primary Examiner*—Mark L. Bell
*Assistant Examiner*—Patricia L. Hailey
(74) *Attorney, Agent, or Firm*—Robert A. Koons, Jr.; Pepper Hamilton LLP

(57) ABSTRACT

Alkanes are converted to unsaturated carboxylic acids by contacting an alkane with an oxidizing agent and a Wells-Dawson type heteropolyacid supported on wide pore polyoxometallate salts.

17 Claims, 2 Drawing Sheets

OTHER PUBLICATIONS

Cavani, et al., "Enhancement of Catalytic Activity of the Ammonium/Postassium Salt of 12–Molybdophosphoric Acid by Iron Ion Addition for the Oxidation of Isobutane to Methacrylic Acid." *Catalysis Letters*, vol. 32, pp. 215–226, (1995). Feb. 1985.

G. Centi, et al., "Selective Oxidation of Light Alkanes: Comparison Between Vanadyl Pyrophosphate and V–Molybdophosphoric Acid." *Catal. Sci. Technol., Proc. Tokyo Conf.*, 1st Meeting pp. 225–230, Jul. (1990).

Domaille, et al., "Synthesis and $^{183}$W NMR Characterization of Vanadium–Substituted Polyoxometallates Based on B–typ $PW_9O_{34}{}^{9-}$–Precursors." *Inorg. Chem.*, vol. 25, pp. 1239–1242, (1986). Oct. 1985.

Finke, et al., "Trisubstituted Heteropolytungstates as Soluble Metal Oxide Analogues $3^1$. Synthesis, Characterization, $^{31}$P, $^{29}$Si, $^{51}$V, and 1 –2–D $^{183}$W NMR, Deprotonation and H$^+$ Mobility Studies of Organic Solvent Soluble Forms of $H_xSiW_9V_3O_{40}{}^{x-7}$." *J. Ameri. Chem. Soc.*, vol. 108, pp. 2947–2960, (1986), Aug. 1985.

Mizuno, et al., "Direct Oxidation of Isobutane into Methacrylic Acid and Methacrolein over Cs $_{2.5}Ni_{0.08}$–substituted $H_3PMo_{12}O_{40}$." *J. Chem. Soc., Chem. Commun.*, pp. 1411–1412, Feb. 1994.

N. Mizuno, et al., "Synthesis of $[PW_9O_{37}\{Fe_{3-x}Ni_{x(}OAc_3\}]^{(9-x)-}$(x=predominantly 1) and Oxidation Catalysis by the Catalyst Precursors." *J. Mol. Cat.*, vol. 88, L125–31, (1994). Dec. 1973.

Mizuno, et al., "Catalytic Performance of $Cs_{2.5}Fe_{0.08}H_{1.26}PVMo_{11}O_{40}$ for Direct Oxidation of Lower Alkanes." J. Mol. Catal., A, vol. 114 pp. 309–317, (1996). Month N/A.

Mizuno, et al. "Pronounced Catalytic Activity of $Fe_{0.08}Cs_{2.5}H_{1.26}PVMo\ 11_{11}O_{40}$ for direct oxidation of propane into acrylic acid." *Applied Catalysts A*: General, vol. 128, L165–L170, Feb. 1995.

Fernando Ortega, Ph.D., Thesis, Georgetown University, Mar. (1982).

Pope, et. al., "Heteropoly and Isopoly Oxometalates," Springer–Verlag, pp. 17–18, and 31–32, New York 1983 month N/A.

F, Trifiro, "Reactivity of Keggin–type Heteropolycompounds in the Oxidation of Isobutane to Methacrolein and Methacrylic Acid: Reaction Mechanism." *J. Mol. Catal.*, A, vol. 114, pp. 343–359, (1996). month N/A.

Ueda, et al., "Catalytic Oxidation of Isobutane to Methacrylic acid with molecular Oxygen Over Activated Pyridinium 12–Molybdophosphate." *Cat. Lett.*, vol. 46, pp. 261–265, May 1997.

Ueda, et al., "Partial Oxidation of Propane to Acrylic Acid over Reduced Heteropolymolybdate catalysts." *Chemistry Letters*, vol. 541–2 Apr. 1995.

Uemura, et al. "Oxotrimetal Acetato–complexes of Chromium, Manganese, Iron, Cobalt, Rhodium, and Iridium." *J. Chem. Soc. Dalton Trans.*, pp. 2565–2571, (1973). month N/A.

Wu, et al., "Catalytic Behaviour of Metal Ions Located at Different Site of Heteropoly Compounds." *Catlysis Letters*, vol. 23, pp. 195–205, (1994). Aug. 1993.

Abbessi, Mostefa, et al. "Dawson Type Heteropolyanions. 1. Multinuclear ($^{31}$P $^{51}$V, $^{183}$W) NMR Structural Investigations of Octadeca (molybdotungstovanado) diphosphates α–1,2, 3–$[P_2MM'_2\ W_{15}O_{62}]^{n-}$(M,M'=Mo, V, W): Sytheses of New Related Compounds" *Inorg. Chem. 30*, pp. 1695–1702, (1991). Jun. 1990.

Böttcher, Arnd, et al. Aerobic oxidation of hydrocarbons catalyzed by electronegative iron salen complexes. *Journal of Molecular Catalysis A: Chemical 113 pp. 191–200*, Jan. (1996).

Ciabrini, J.P., et al. "Heteropolyblues: Relationship Between Metal–Oxygen–Metal Bridges and Reduction Behaviour of Octadeca (Molybdotungsto) Diphosphate Anions." *Polyhedrom vol. 2 No. 11 pp. pp. 1229–1233*, Jun. (1983).

Comuzzi, Clara, et al. "The solid–state rearrangement of the Wells–Dawson $K_6P_2W_{18}O_{62}$–10H$_2$O to a stable Keggin–type heteropolyanion phase: a catalyst for the selective oxidation of isobutane to isobutene" *Catalysis Letters 36 pp. 75–79*, (1996). Sep. 1995.

Finke, Richard G., Trivacant Heterpolytungstate Derivtives. $3^1$. Rational Syntheses, Characterization, Two–Dimensional $^{183}$W NMR, and Properties of $P_2W_{18}M_4\ (H_2O)_2O_{68}{}^{10-}$ and $P_4W_{30}M_4(H_2O)_2O_{112}{}^{16-}$(M=Co, cu, Zn) *Inorg. Chem.*, 26, pp. 3886–3896, May (1987).

Hill, Craig L. et al. "Homogeneous catalysis by transition metal oxygen anion clusters" *Coordination Chemistry Reviews 143*, pp. 407–455 Feb. (1995).

Lyons, James E., et al. Highly Oxidation Resistant Inorganic–Porphyrin Analogue Polyoxometalate Oxidation Catalysts. 1. The Syntheses and Characterization of Acqueous–Soluble Potassium Salts of $α_2\_P_2W_{17}O_{61}(M^{N+}.OH_2)^{(n-10)}$ and Organic Solvent Soluble Tetra–N–butylammonium Salts of $α_2\_P_2W_{17}O_{61}(M^{n+}.Br)^{(n-11)}$ M=M$^{n3+}$, Fe$^{3+}$, Co$^{24}$,Ni$^{2-}$, Cu$^{2-}$) *J. Am. Chem. Soc.* 113, pp. 7209–7221, (1991). Jan. 1991.

Lyons, James E., et al. Halogenated Metalloporphyrin Complexes as Catalysts for Selective Reactions of Acyclic Alkanes with Molecular Oxygen. *Journal of Catalysis 155*, pp. 59–73, (1995). Feb. 1995.

Wijesekera, Tilak P., et al. "Perfluoroalkylporphyrin complexes as active catalysts for the reaction of isobutane with oxygen and the decomposition of tert–butyl hydroperoxide" Catalysis Letters 36 pp. 69–73, (1996). Sep. 1995.

Wu, Hsein "Contribution to the Chemistry of Phosphomolybdic Acids, Phosphotungstic Acids, and Allied Substances" From the Biochemical Laboratory of Harvard Medical School, Boston. (Received for publication, Jun. 10, 1920), pp. 189–220.

WELLS-DAWSON TYPE HETEROPOLYACIDS, THEIR PREPARATION AND USE AS OXIDATION CATALYSTS

This application is a division of application Ser. No. 09/135,409, filed Aug. 14, 1998, now U.S. Pat. No. 6,060,419, which is a continuation-in-part of applications Ser. No. 09/002,816, filed Jan. 5, 1998, now U.S. Pat. No. 6,043,184, and Ser. No. 09/002,845, filed Jan. 5, 1998, now U.S. Pat. No. 5,990,348.

FIELD OF THE INVENTION

This invention relates to compositions comprising Wells-Dawson type heteropolyacids on supports, such as wide pore polyoxometallate salts, methods for the preparation of such compositions, and the use of supported Wells-Dawson type heteropolyacids for the direct catalytic oxidation of alkanes to unsaturated carboxylic acids.

BACKGROUND OF THE INVENTION

Polyoxometallates and heteropolyacids, both in general and those which can be used to prepare some of the catalysts used in our invention, and their preparation are described in Pope et al., *Heteropoly and Isopoly Oxometalates*, Springer-Verlag, N.Y. (1983).

Polyoxometallates and heteropolyacids consist of a polyhedral cage structure or framework bearing a negative charge (e.g., $[PMo_{12}O_{40}]^{-3}$; $[P_2Mo_{18}O_{62}]^{-6}$) which is balanced by cations that are external to the cage. If the cations are protons, then the compound is a heteropolyacid (UPA) (e.g., $H_6[P_2Mo_{18}O_{62}]$). If the cations were not all hydrogen, but either metals such as an alkali metal, potassium, sodium, or lithium, as in $K_6P_2W_{18}O_{62}$, or ammonium, as in $(NH_4)_6P_2Mo_{18}O_{62}$, then it is referred to as a polyoxometallate (POM). In earlier patents, we have used the term "polyoxoanion" to describe compounds in which some or all of the cations are not hydrogen (e.g., $K_3PMo_{12}O_{40}$); in the present case, however, these compounds are referred to as polyoxometallates and the term polyoxoanion is reserved for describing the anionic cage-like portion of the compound (e.g., $[P_2Mo_{18}O_{62}]^{-6}$)

As described in Pope et al., supra, heteropolyacids and polyoxometallates are cage-like structures with a primary, generally centrally located atom(s) surrounded by a cage framework, which framework contains a plurality of metal atoms, the same or different, bonded to oxygen atoms. The central element of heteropolyacids and polyoxometallates is different from metal atoms of the framework and is sometimes referred to as the "hetero" element or atom, the condensed coordination elements are referred to as the "framework" elements or metals. The framework metal atoms are ordinarily transition metals. As described by Pope et al., sltpra, the majority of heteropolyacids and polyoxometallates have a centrally located heteroatom ("X") usually bonded in a tetrahedral fashion through four oxygen atoms to the "framework" metals ("M"). The framework metals, in turn, (i) are usually bonded to the central atom in an octahedral fashion through oxygens ("O"), and (ii) are bonded to four other framework metals through oxygen atoms and (iii) have a sixth non-bridging oxygen atom known as the "terminal oxygen" atom. This can be illustrated as shown below:

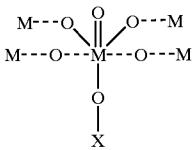

The principal framework metal, M, is effectively limited to only a handful of metals including molybdenum, tungsten, vanadium niobium and tantalum. According to Pope et al., supra, this is due to the necessary condition that suitable metals have appropriate cation radius and be good oxygen pπ-electron acceptors. Among the successful candidates, molybdenum and tungsten share a common feature; namely, the expansion of valences of their metal cations from four to six. The coincidence of these characteristics allow these metals to form stable heteropolyacids and polyoxometallates.

Conventional heteropolyacids (and polyoxoanions thereof) can be described by the general formula $H_e(X_kM_nO_y)^{-e}$. In this formula, X, the central atom, is frequently phosphorus. However, other suitable central atoms include Group IIIB–VIB elements, such as antimony, silicon and boron. Further, the subscript k is preferably 2, but can be from 1 to 5. M is molybdenum, tungsten, or vanadium and n will vary from 5–20. The subscript y may be as low as 18 or as high as 62. The notation e is the negative charge on the $(X_kM_nO_y)$ polyoxoanion and will vary from case to case, but e is always the number of protons needed to balance the formula. In a typical such heteropolyacid, k=2, n=18 and y=62, as in $H_6P_2Mo_{18}O_{62}$ and the polyoxometallate $H_2(VO)_2[P_2Mo_{18}O_{62}]$.

As described in Pope et al., supra, heteropolyacids are known to exist in a variety of structures including the Keggin, Wells-Dawson and Anderson structures. The different structures correspond to the specific geometry of particular heteropolyacid compositions and vary according to the coordination chemistry and atomic radii of the metals present. These compounds may be substituted at various framework sites as disclosed, inter alia, in our prior patents. The present invention focuses on compounds of the Wells-Dawson type structure.

In our U.S. Pat. No. 4,803,187, issued Feb. 7, 1989, we taught how to prepare heteropolyacids and polyoxometallates with random substitution of framework metals, such as $H_7(PMo_8V_4O_{40})$; $K_6(SiMo_{11}MnO_{39})$ and $K_5(PW_{11}VO_{40})$. The preparation of framework-substituted heteropolyacids or polyoxometallates as described in our U.S. Pat. No. 4,803,187, supra, is adequate for random substitution, but will not provide the regiospecific, trilacunary substitution as described in our U.S. Pat. No. 4,898,989, supra; i.e., replacement of three M in a single, triangular face with three M'. The teaching of U.S. Pat. No. 4,803,187 and U.S. Pat. No. 4,898,989 is incorporated for all purposes by reference herein.

As described in Pope et al., supra, heteropolyacids and polyoxometallates have found a variety of applications. In the area of catalysis, Keggin ion catalysts have been used in connection with the oxidation of propylene and isobutylene to acrylic and methacrylic acids, oxidation of aromatic hydrocarbons; olefin polymerization; olefin epoxidation, and hydrodesulfurization processes. See, for example, M. Ai, "Partial Oxidation of n-Butane with Heteropoly Compound-based Catalysts", *Proceedings of the 18th International Congress on Catalysis*, Berlin, 1984, Verlag Chemie, Vol. 5, page 475; Lyons et al., U.S. Pat. No. 4,803,187, issued Feb. 7, 1989; Lyons et al., U.S. Pat. No. 4,859,798, issued Aug. 22, 1989; Ellis et al., U.S. Pat. No. 4,898,989, issued Feb. 6, 1990; Lyons et al., U.S. Pat. No. 4,916,101, issued Apr. 10, 1990; Ellis et al., U.S. Pat. No. 5,091,354, issued Feb. 25, 1992; and Shaikh et al., U.S. Pat. No. 5,334,780, issued Aug. 2, 1994; each of which is incorporated herein by reference.

Framework-substituted Keggin heteropolyacids have been disclosed as catalysts for oxidation of aldehydes, cyclohexene and cyclohexane, and for hydrogen peroxide decomposition. N. Mizuno et al., "Synthesis of $[PW_9O_{37}\{Fe_{3-x}Ni_x(OAc)_3\}]^{(9+x)-}$ (x=predominantly 1) and Oxidation Catalysis by the Catalyst Precursors", *J.Mol.Cat.*, 88, L125–31 (1994); and Wu et al., "Catalytic Behavior of Metal Ions Located at Different Sites of Heteropoly Compounds", *Catalysis Letters*, 23, 195–205 (1994).

Non-framework substituted Keggin polyoxometallates and heteropolyacids are known in the art as catalysts for oxidation of isobutane to methacrylic acid and methacrolein. W. Ueda et al., "Catalytic Oxidation of Isobutane to Methacrylic Acid with Molecular Oxygen over Activated Pyridinium 12-Molybdophosphate", *Cat.Lett.*, 261–265 (1997); N. Mizuno et al., "Catalytic Performance of $Cs_{2.5}Fe_{0.08}H_{1.26}PVMo_{12}O_{40}$ for Direct Oxidation of Lower Alkanes", *J.Mol.Catal.*, A, 114, 309–317 (1996); F. Trifiro et al., "Reactivity of Keggin-type Heteropolycompounds in the Oxidation of Isobutane to Methacrolein and Methacrylic Acid: Reaction Mechanism", *J.Mol.Catal.*, A, 114, 343–359 (1996); N. Mizuno et al., "Direct Oxidation of Isobutane into Methacrylic Acid and Methacrolein over $Cs_{2.5}Ni_{0.08}$-substituted $H_3PMo_{12}O_{40}$", *J.Chem.Soc.,Chem.Commun.*, 1411–1412 (1994); S. Yamamatsu et al., "Process for Producing Methacrylic Acid and Methacrolein", European Patent Specification Publication No. 0 425 666 B1, Application No. 89905775.6 filed May 22, 1989, Date of publication of patent specification Apr. 13, 1994; S. Yamamatsu et al., "Method for the Fabrication of Methacrylic Acid and/or Methacrolein", Japanese Patent Application Public Disclosure No. H2-42034, Feb. 13, 1990; S. Yamamatsu et al., U.S. Pat. No. 5,191,116, issued Mar. 2, 1993; K. Nagai et al., Process for producing methacrylic acid and methacrolein by catalytic oxidation of isobutane", European Patent Application Publication No. 0 418 657 A2, Application No. 90117103.3, filed Sep. 5, 1990 by Sumitomo Chem.Ind.KK (published Mar. 27, 1991); T. Jinbo et al., "Method for the Manufacture of Acroleic Acid or Acrylic Acid, and Catalysts Used Therein", Japanese Patent Application Public Disclosure No. H6-218286, Aug. 9, 1994; M. Ai, "Partial Oxidation of n-Butane with Heteropoly Compound-based Catalysts", Labo. Resources Utiliz., Tokyo Inst. Tech., Yokohama, Japan, *8th International Congress on Catalysis, Volume V: Cluster-derived catalysts, Active phase support interactions, Catalysts for synthesis of Chemicals*, Verlag Chemie, Berlin, pages V475–V486 (1984); G. Centi et al., "Selective Oxidation of Light Alkanes: Comparison between Vanadyl Pyrophosphate and V-Molybdophosphoric Acid", Catal.Sci.Technol., *Proc. Tokyo Conf.*, 1st Meeting, 1990, 225–30; N. Mizuno et al., "Catalytic Performance of $Cs_{2.5}Fe_{0.08}H_{1.26}PVMo_{11}O_{40}$ for Direct Oxidation of Lower Alkanes", *J.Mol.Catal.*, A, 114, 309–317 (1996); M. Ai, "Oxidation of Propane to Acrylic Acid", *Catalysis Today*, 13 (4), 679–684 (Eng.) (1992); N. Mizuno et al., *Applied Catalysis A: General*, 128, L165–L170 (1995); Ueda et al., *Chemistry Letters*, 541, 2 (1995); Cavani et al., *Catalysis Letters*, 32 215–226 (1995).

The references cited above primarily employed non-framework substituted Keggin-type heteropolyacids as catalysts in manufacture of unsaturated carboxylic acids, for example acrylic acid and methacrylic acid, from alkanes, for example propane and isobutane. There is no known use of Wells-Dawson-type heteropolyacids for catalysis of these reactions.

Wells-Dawson-type heteropolyacids are more difficult to prepare than the Keggin compounds. This may explain the paucity of published works regarding their activity. In fact, work relating to Wells-Dawson structures is primarily limited to their use for certain homogeneous liquid-phase reactions (Hill, et al., *Coord.Chem.Rev.*, 143, 407 (1995)) and in the decomposition of hydrogen peroxide (Wu, et al., *Cat.Lett.*, 23, 195 (1994)). Comuzzi et al., *Cat.Lett.*, 36, 75 (1996), investigated the gas-phase oxidative dehydrogenation of isobutane to isobutene catalyzed by $K_6P_2W_{18}O_{62}$, a Wells-Dawson-type phosphotungstate. However, despite the literature on Keggin-type compounds, there has been no disclosure of the use of the acid form of the Wells-Dawson-type compounds (i.e., $H_e(P_2M_{18}O_{62})^{-e}$) or use of Wells-Dawson-type phosphomolybdates (e.g., $K_6P_2Mo_{18}O_{62}$), for example, for the heterogeneous gas-phase oxidation of alkanes to unsaturated carboxylic acids.

Given the value and industrial importance of acrylic acid and methacrylic acid, it has been recognized that the one-step conversion of alkanes to unsaturated carboxylic acids would be a useful process with important commercial applications, provided that sufficient yield can be obtained. To date, no efficient catalysts have been developed for the commercial production of acrylic acid from propane or methacrylic acid from isobutane. As a result, acrylic acid is manufactured from propylene, a raw material which is over three times more expensive than propane.

The process of the present invention provides such a one-step process for the conversion of alkane to carboxylic acid catalyzed by Wells-Dawson type HPAs. These catalysts have been found to yield superior results to Keggin-type HPAs having similar metals. Through electrochemical experiments, we have demonstrated that Wells-Dawson HPAs have superior redox properties to Keggin HPAs. At the same time, we have found that Wells-Dawson HPAs are more efficient catalysts for the oxidation of alkanes to α-β-unsaturated oxidation products than Keggin HPAs in comparable experiments. These advantages make the process more attractive than the prior art processes for practical use and potential commercial interest.

SUMMARY OF THE INVENTION

The present invention relates to the oxidation of alkanes to unsaturated carboxylic acids or nitriles catalyzed by supported or unsupported, fully or partially protonated Wells-Dawson-type polyoxoanions (heteropolyacids (HPAs)) which may also have been promoted or otherwise modified to improve their effectiveness. The support is preferably a wide pore cation salt of a heteropolyacid (polyoxometallate (POM)), for example, a wide pore polyoxometallate salt, but other supports are also suitable for use according to the invention. The process of the invention is useful, for example, for the conversions of propane to acrylic acid or acrylonitrile, and isobutane to methacrylic acid or methacrylonitrile. In one embodiment, the process of the present invention involves the conversion of alkane to unsaturated carboxylic acid at a temperature in the range of about 225° C. to 450° C. by contacting the alkane with an oxidizing agent in the presence of a supported Wells-Dawson-type heteropolyacid catalyst, where the support comprises a wide pore cesium heteropolyoxometallate salt.

The process of the invention is also applicable to the conversion of alkanes to unsaturated nitriles.

The invention comprises a process for the conversion of alkanes to unsaturated carboxylic acids which comprises contacting an alkane with an oxidizing agent under oxidation conditions with a Wells-Dawson type heteropolyacid (HPA) supported on a wide-pore polyoxometallate (POM). Thus the catalyst of this process can be defined as a HPA/POM catalyst. The HPA component of the catalysts useful in the process of the present invention has the general formula:

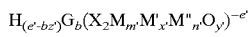

$$H_{(e'-bz')}G_b(X_2M_mM'_{x'}M''_{n'}O_{y'})^{-e'}$$

where G is Cu, Fe, Co, Mn, Ni, La, Li, Na, K or Rb, or an oxy ion of Ti, V, Cr, Mo, U, As, Bi, Sb, Nb, or ammonium, tetraalkylammonium, pyridinium, quinolinium, protonated aromatic amines or protonated aliphatic amines, or combinations thereof, or is absent; X is a Group IIIB, IVB, VB, VIB or transition element, such as phosphorus, silicon, gallium, aluminum, arsenic, germanium, boron, cobalt, cerium, praseodymium, uranium and thorium; M is molybdenum or tungsten, or combinations thereof, M' is vanadium; M" is independently zinc or a transition metal different from M and M', such as titanium, zirconium, hafnium, niobium, tantalum, chromium, manganese, rhenium, iron, cobalt, nickel, ruthenium, rhodium, palladium, osmium, iridium, platinum, copper or combination thereof, z' is the charge on said cation G; m' is 12 to 18, x' is 0 to 6, n' is 0 to 3, where m'+x'+n'=18; y' is 48 to 62; and e' is the charge of the anion of the polyoxometallate. The support component comprises an insoluble polyoxometallate salt having the formula:

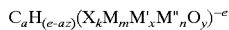

$$C_aH_{(e-az)}(X_kM_mM'_xM''_nO_y)^{-e}$$

where cation C is selected from the group consisting of potassium, rubidium, cesium, magnesium, calcium, strontium, barium, vanadium, chromium, lanthanum, manganese, iron, cobalt, ruthenium, copper, actinide metal, lanthanide metal, metal oxy ion, ammonium, tetraalkylammonium, pyridinium, quinolinium, protonated aromatic amines and protonated aliphatic amines, or combinations thereof; X is a Group IIIB, IVB, VB, VIB or transition metal; M is molybdenum or tungsten or combinations thereof; M' is vanadium; M" is independently zinc or a transition metal different from M and M', or combination thereof; z is the charge on said cation C; k is 1 to 5, m is 5 to 18, x is 0 to 6, n is 0 to 3, y is 18 to 62.

A preferred cation for the POM support is cesium; for example, $Cs_{3+x}(PMo_{12-x}V_xO_{40})$, where x is 0 to 2. Thus, the HPA/POM catalysts which have been found to be effective have the general formula:

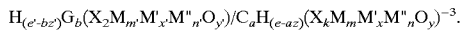

$$H_{(e'-bz')}G_b(X_2M_mM'_{x'}M''_{n'}O_{y'})/C_aH_{(e-az)}(X_kM_mM'_xM''_nO_y)^{-3}.$$

An example of an HPA/POM catalyst is $H_6(P_2Mo_{18}O_{62})/Cs_3(PMo_{12}O_{40})$. In one embodiment, the POM support comprises a combination of two POMs, for example, a Cs-POM and a K-POM; e.g., $Cs_3(PMo_{12}O_{40})$ and $K_6(P_2W_{18}O_{62})$.

The conversion process is carried out at a temperature in the range from 225° C. to 450° C., preferably in the range from 350° C. to 400° C. The pressure used in the process of the invention is not critical and may, for example, be atmospheric pressure or such other pressure as is within the ability of the person skilled in the art to determine.

DETAILED DESCRIPTION OF THE INVENTION

Figure 1:
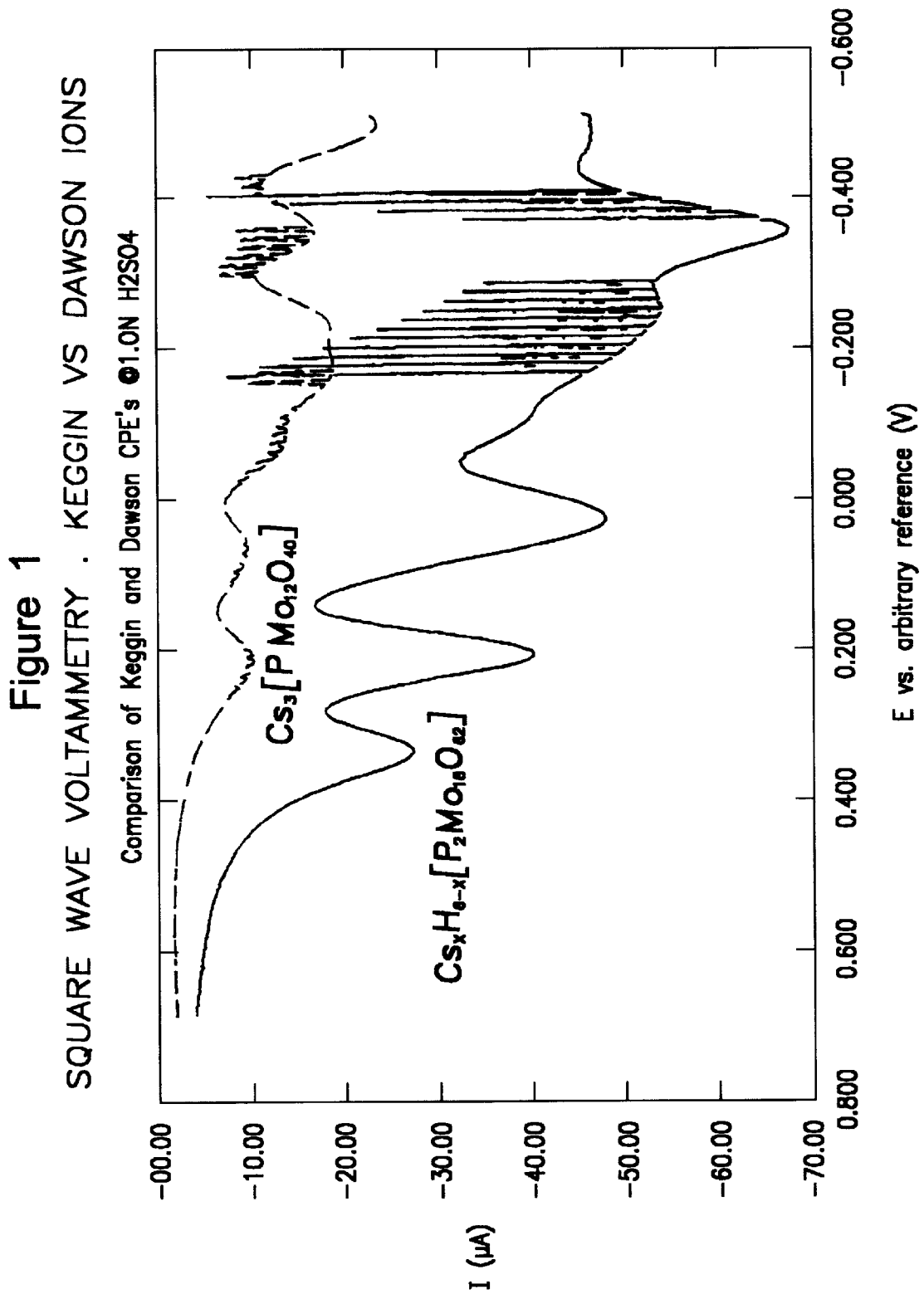
FIG. 1 shows the relative reduction potential of framework metals of a Wells-Dawson-type HPA and a Keggin-type HPA.

The present invention relates to the oxidation of alkanes to unsaturated carboxylic acids or nitriles catalyzed by heteropolyacids (HPAs) supported on wide pore polyoxometallates (POMs) which may have been promoted or otherwise modified to improve their effectiveness. The process of the invention is useful, for example, for the conversions of propane to acrylic acid or acrylonitrile and isobutane to methacrylic acid or methacrylonitrile.

Reaction Conditions

The temperature used in the process of the invention is that which favors the formation of unsaturated carboxylic acids or nitriles as reaction products. The conversion process is generally carried out at a temperature in the range from about 225° C. to about 450° C., preferably at a temperature in the range from about 350° C. to 400° C. Notwithstanding this, certain catalysts within the scope of the present invention, particularly those HPAs supported on phosphotungstate Keggin ion (e.g., $Cs_3(PW_{12}O_{40})$) have been found to maintain their physical and structural integrity at temperatures up to approximately 500° C. These catalysts in particular may be used in the oxidation process of the present invention at temperatures in the range of 350° C. to 500° C. where propane activation occurs more readily. The determination of the most desirable temperature for a given reaction and given catalyst within the scope of the invention is within the ability of the person skilled in the art.

The process may be carried out at atmospheric pressure. Other pressures may be used, and the determination of the most desirable pressure for a given reaction within the scope of the invention is within the ability of the person skilled in the art.

The process of the invention may be carried out in any suitable reactor configuration. For example, the reaction may be performed in a fixed-bed, moving bed, ebullating bed reactor, or other as is within the ability of the person skilled in the art to determine.

The process of the invention is preferably carried out in vapor phase. Preferably, the feedstock is an alkane gas. The reaction may be carried out in the presence or absence of steam. An inert gas, such as nitrogen, argon, helium or the like, may also be used. When an inert, diluting gas is used in the process of the invention, determination of the molar ratio of alkane, oxidant, diluting gas and water (steam), if present, in the starting reaction gas mixture is within the ability of the skilled practitioner in the art. Determination of the gas space velocity used in the process of the invention is within the ability of the skilled practitioner in the art.

Feedstocks

The alkane starting materials include straight and branched-chain compounds suitable for conversion to unsaturated carboxylic acids or combinations thereof, or to unsaturated nitriles or combinations thereof. Preferred among these are light alkanes comprising three to seven carbon atoms. More preferred feedstocks for the process of the present invention are propane and isobutane which may be oxidized by the process of the present invention to form acrylic acid and methacrylic acid, respectively, or, when ammonia is present in the feed, to form acrylonitrile and methacrylonitrile, respectively.

As noted above, the feedstock may comprise a combination of alkanes, preferably $C_3$–$C_7$ alkanes. In addition, the purity of the starting material is not critical, though it is preferable to avoid the presence of compounds which may poison the catalyst. As a result, the feedstock may, in addition to the alkane or alkanes of interest, further comprise methane or ethane as well as impurities such as air or carbon dioxide.

Suitable oxidants for use in the process of the invention comprise air, molecular oxygen and other oxidants, such as nitrogen oxides. Preferred among these are air and molecular oxygen.

In one embodiment of the invention, an alkane is contacted with an oxidizing agent in the presence of a supported Wells-Dawson heteropolyacid catalyst. For example propane is contacted with an oxidizing agent in the presence of a supported Wells-Dawson heteropolyacid catalyst according to the invention, to produce acrylic acid. Similarly, isobutane is converted to methacrylic acid. The support comprises a wide pore polyoxometallate salt. The supported heteropolyacid may be framework-substituted as described elsewhere herein.

Catalyst

The catalysts useful in the process of the present invention comprise supported Wells-Dawson type heteropolyacids. Effective catalysts comprise Wells-Dawson HPAs on a support comprising at least one wide-pore polyoxometallate. These catalysts are novel compositions of matter. The soluble heteropolyacid component of the catalysts useful in the process of the present invention has the general formula:

where cation G is $Cu^{++}$, $Fe^{+++}$, Co, Mn, Ni, La, Li, Na, K or Rb, or an oxy ion of Ti, V, Cr, Mo, U, As, Bi, Sb, Nb, or ammonium, tetraalkylammonium, pyridinium, quinolinium, protonated aromatic amines or protonated aliphatic amines, or combinations thereof, or is absent; X is a Group IIIB, IVB, VB, VIB or transition element, such as phosphorus, silicon, gallium, aluminum, arsenic, germanium, boron, cobalt, cerium, praseodymium, uranium and thorium; M is molybdenum or tungsten, or combinations thereof; M' is vanadium; M" is independently zinc or a transition metal different from M and M', such as titanium, zirconium, hafnium, niobium, tantalum, chromium, manganese, rhenium, iron, cobalt, nickel, ruthenium, rhodium, palladium, osmium, iridium, platinum, copper or combination thereof, z' is the charge on said cation G; m' is 12 to 18, x' is 0 to 6, n' is 0 to 3, where m'+x'+n'=18, y' is 48 to 62; and e' is the charge of the anion of the polyoxometallate.

The catalysts used in the process of the invention are heteropolyacids supported on at least one wide pore polyoxometallate salt. A preferred support comprises an insoluble polyoxometallate salt having the formula:

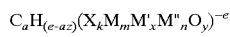

where cation C is selected from the group consisting of potassium, rubidium, cesium; magnesium, calcium, strontium, barium; transition metal, such as vanadium, chromium, lanthanum, manganese, iron, cobalt, ruthenium, copper and the like; actinide metal; lanthanide metal; metal oxy ion, such as oxy ions of vanadium, chromium and uranium and the like; ammonium, tetraalkylammonium, pyridinium, quinolinium, protonated aromatic amines and protonated aliphatic amines, or combinations thereof, X is a Group IIIB, IVB, VB, VIB or transition metal, M is molybdenum or tungsten or combinations thereof; M', is vanadium; M" is independently zinc or a transition metal different from M and M', or combination thereof, z is the charge on said cation C; a is the number of cations C, e is the charge of the anion of the polyoxometallate k is 1 to 5, m is 5 to 18, x is 0 to 6, n is 0 to 3, y is 18 to 62. When "az" equals "e", then there are no protons present in the polyoxometallate support.

Suitable cations in the POMs useful in the process of the invention comprise alkali metal, including, but not limited to, potassium, sodium, cesium and the like; magnesium, calcium, strontium, barium; transition metal, such as vanadium, chromium, lanthanum, manganese, iron, cobalt, ruthenium, copper and the like; actinide metal; lanthanide metal, metal oxy ion, such as oxy ions of vanadium, chromium and uranium and the like, for example, vanadyl, chromyl, uranyl and the like; or other cation such as ammonium, $R_4N^+$ ("tetraalkylammonium") and the like; pyridinium, quinolinium and protonated aromatic amines and protonated aliphatic amines. Of these cations, preferred cations comprise potassium, rubidium, cesium, magnesium, calcium, strontium, barium, lanthanum, ammonium, tetraalkylammonium, pyridinium, quinolinium, protonated aromatic amines and protonated aliphatic amines, or combinations thereof. The presence of vanadyl has been found to result in a particularly effective compound.

A preferred cation for the support POM is cesium; for example, $Cs_{3+x}(PMo_{12-x}V_xO_{40})$, where x is 0 to 3. Preferred embodiments of the support include $Cs_3(PMo_{12}O_{40})$, $Cs_4(PMo_{11}VO_{40})$, $Cs_5(PMo_{10}V_2O_{40})$, $Cs_3(PW_{12}O_{40})$, $Cs_6(P_2Mo_{18}O_{62})$, $Cs_6(P_2W_{18}O_{62})$, or combinations thereof. Other suitable supports include wide pore salts, for example wide pore cesium salts of the various substituted polyoxometallates described below and in Lyons et al., U.S. Pat. No. 5,705,685, issued Jan. 6, 1998, which is incorporated by reference herein for all purposes. The support for the catalyst may comprise more than one POM composition; for example, the support may comprise a mixture of two or more POMs; for example, a Cs-POM and a K-POM; e.g, $Cs_3(PMo_{12}O_{40})$ and $K_6(P_2W_{18}O_{62})$. Other suitable supports comprise silicas, silicalites, zeolites, aluminas and the like, preferably coated on with a suitable POM of the types described herein.

The support is a porous material having pore volumes in the range from 0.01 to 0.25 ml/g and a pore size distribution in which more than approximately 60% of the pores have a pore radius of greater than or equal to approximately 75 Å, preferably greater than or equal to approximately 100 Å, more preferably greater than or equal to approximately 150 Å, still more preferably greater than or equal to approximately 200 Å. More preferably, the support has pore volumes in the range from 0.05 to 0.25 ml/g and a pore size distribution in which more than approximately 60% of the pores have a pore radius of greater than or equal to approximately 75 Å. In a preferred embodiment, the support material has pore volumes in the range from 0.01 to 0.25 ml/g and a pore size distribution in which more than approximately 80% of the pores have a pore radius of greater than or equal to approximately 200 Å; more preferably, the support material has pore volumes greater than 0.15 ml/g and a pore size distribution in which more than approximately 80% of the pores have a pore radius of greater than approximately 250 Å.

Preferably, the pores in the support have pore radii of greater than 75 Å and pore volumes greater than 0.05 ml/g;

more preferably, the pore radii are greater than 100 Å, and independently, the pore volumes are greater than 0.1 ml/g. It has been found that supports with pore volumes greater than 0.02 ml/g result in catalysts with superior activity, provided the pores are wide (i.e., radii greater than approximately 75 Å). These supported catalysts may be further modified by pretreatment with water and by formation in the presence of vanadyl acetylacetonate or $VOSO_4$.

Typically, the POM support component of the catalyst may be prepared by adding a soluble salt of the desired cation, for example $Cs_2CO_3$ or $CsNO_3$ or the like for a cesium salt support, to the desired soluble heteropolyacid, for example $H_3(PMo_{12}O_{40})$, to form the insoluble POM, for example $Cs_3(PMo_{12}O_{40})$. The salt solution is preferably added slowly into the heteropolyacid solution to precipitate the cation heteropolymetallate salt. The following reactions exemplify the process:

$$3Cs_2CO_3 + 2H_3(PMo_{12}O_{40}) \rightarrow 2Cs_3(PMo_{12}O_{40}) + 3H_2O + 2CO_2$$

$$3Cs_2CO_3 + H_6(P_2Mo_{18}O_{62}) \rightarrow Cs_6(P_2Mo_{18}O_{62}) + 3H_2O + 3CO_2$$

The precipitation may be performed at an elevated temperature (e.g., 25–100° C.) and $CO_2$ is evolved during the reaction. The resulting POM salt forms a fine suspension in water and may be evaporated to dryness, for example by rotary evaporation, or by heating at 50° C. or below. The dried material may be calcined (e.g., at 275° C.). POMs having the formula $Cs_aH_{(e-a)}(X_kM_{m-x}M'_xM''_nO_y)^{-e}$, as described more fully herein, may be prepared according to this process.

After calcination, the physical properties of the POM salt may be determined, for example the surface area, the pore volume and the pore size distribution (PSD). It has been found that the preparation process can influence these physical characteristics. For example, slow addition of the cation salt to the HPA solution results in a material with few small pores and many large pores. In contrast, rapid addition of the cation salt yields a broad PSD with many small pores and some intermediate and large pores. For the present invention, slow addition to form mainly wide pores is preferable; for example, at a rate of 2 ml/minute, particularly when using solution concentrations of approximately 0.1 mole/liter. More generally, the salt solution may have a concentration in the range from approximately 0.05 to 1 mole/liter, preferably 0.1 to 0.2 mole/liter, and the HPA solution may have a concentration in the range from approximately 0.05 to 1 mole/liter, preferably 0.1 to 0.2 mole/liter, and more preferably 0.1 mole/liter. The solutions may be mixed at a rate in the range from 0.5 to 20 ml/minute, preferably 1 to 10 ml/minute, more preferably 2 ml/minute. More preferably, particularly for the preparation of large quantities of material, the solutions of the cation salt and the HPA may be added simultaneously to a reaction vessel.

A further factor influencing the PSD was found to be the temperature of the reaction medium during the precipitation step. Precipitation at room temperature yielded a narrow PSD with a median pore radius of about 90 Å, whereas precipitation at 65° C. was found to result in a broader PSD with a greater median pore radius ($\geq 120$ Å). The precipitation step may be carried out at a temperature in the range from approximately 25° C. to 100° C.; preferably in the range from 50° C. to 80° C.; more preferably in the range from 60° C. to 65° C.

Additionally, it has been found that aging of the slurry containing the polyoxometallate salt, followed by slow evaporation to dryness, is beneficial to the production of wide pore materials. Preferably, the slurry is allowed to remain at room temperature or at a temperature in the range from approximately 25° C. to 45° C., preferably 35° C. to 45° C., for an extended period of time and is then slowly dried. The aging and drying process may extend for a period of 12 to 72 hours or longer. This forms a wide-pore material. Finally, use of excess cation salt (relative to the stoichiometric amount) has been found to promote formation of the desired wide-pore support material. While the support material can be prepared using stoichiometric ratios of starting materials, it is preferred to use an excess of the cation salt.

It has been found that certain POM salts, particularly for example $Cs_3(PMo_{12}O_{40})$, are produced with greater pore sizes and pore volumes than certain other comparably prepared materials, such as $Cs_4(PMo_{11}VO_{40})$, $Cs_3(PW_{12}O_{40})$ and $Cs_3(AsMo_{12}O_{40})$. However, we have developed a novel preparation method involving the simultaneous precipitation of $Cs_3(PMo_{12}O_{40})$ along with the desired POM salt which yields materials with comparable pore sizes and pore volumes to the $Cs_3(PMo_{12}O_{40})$ material.

The following procedure has been found to yield POM salts with comparable desirable pore sizes and pore volumes as $Cs_3(PMo_{12}O_{40})$. According to this process, $Cs_3(PMo_{12}O_{40})$ is in solution with the desired salt of $Cs_3(PM_{12-x}M'_xO_{40})$ and is simultaneously precipitated with the desired POM salt. Examples of suitable materials for preparation according to this process include, for example, $Cs_4(PMo_{11}VO_{40})$, $Cs_5(PMo_{10}V_2O_{40})$, $Cs_3(PW_{12}O_{40})$, $Cs_6(P_2Mo_{18}O_{62})$ and $CS_6(P_2W_{18}O_{62})$. In order to precipitate the two POM salts simultaneously, a solution of the two HPAs, or two separate solutions of the two HPAs, are slowly mixed with a solution of the salt of the desired cation, for example $Cs_2CO_3$. The solution concentration, the mixing rate, the reaction temperature and the time of drying and aging of the precipitate are the same as that described above. It is believed that this process is applicable as well to the preparation of other POM salts described herein. For Cs-POM supports of the Wells-Dawson type, lower precipitation temperatures (i.e., room temperature) are preferable.

The Wells-Dawson heteropolyacids supported on such supports comprise heteropolyacids, which may have been framework-substituted as described below. Likewise, the polyoxometallate comprising the support may have been framework-substituted as described below. The substitution may, for example, be monosubstitution, regio-disubstitution or regio-trisubstitution, all of which produce effective compositions for use as the supported HPA and the support POM in the process of the present invention. The catalysts may be further promoted by a variety of means described below. The present invention encompasses unsubstituted and substituted HPAs supported on wide pore salts of unsubstituted and substituted POMs.

In one embodiment, the catalyst, a modified HPA supported on a wide-pore POM as described above, has the general formula:

$$H_{(e'-bz')}G_b(X_2M_{m'}M'_{x'}M''_{n'}O_{y'})^{-e'}/C_aH_{(e-bz)}(X_kM_mM'_xM''_nO_y)^{-e}$$

where, in the HPA $H_{(e'-bz')}G_b(X_2M_{m'-x'}M'_{x'}M''_{n'}O_{y'})^{-e'}$, G, the cation, is Cu++, Fe+++, lithium (Li), sodium (Na), potassium (K), rubidium (Rb), cobalt (Co), manganese (Mn), nickel (Ni), or lanthanum (La), or an oxy ion of titanium (Ti), vanadium (V), chromium (Cr), uranium (U), arsenic (As), bismuth (Bi), tin (Sn), niobium (Nb), or ammonium, tetraalkylammonium, pyridinium, quinolinium, protonated aromatic amines or protonated aliphatic amines, or combinations thereof, or is absent; X, the central or hetero atom, is a Group IIIB, IVB, VB, VIB or transition element, such as phosphorus, silicon, gallium, aluminum, arsenic, germanium, boron, cobalt, cerium, praseodymium, uranium and thorium; M, the first framework metal is molybdenum or tungsten or combinations thereof; M' is vanadium substituted for first framework metal M; M", the second framework metal, is different from M and is independently zinc or a transition metal, such as titanium, zirconium, hafnium, niobium, tantalum, chromium, manganese, rhenium, iron, cobalt, nickel, ruthenium, rhodium, palladium, osmium, iridium, platinum, copper or combination thereof; m' is 12 to 18, x' is 0 to 6, n' is 0 to 3 where m'+x'+n'=18; y' is 48 to 62; e' is the charge of the anion of the heteropolyacid; and z' is the charge on the cation G; and where, in the POM $C_aH_{(e-bz)}(X_kM_mM'_xM''_nO_y)^{-e}$, C is selected from the group consisting of potassium, rubidium, cesium, magnesium, calcium, strontium, barium, lanthanum, ammonium, tetraalkylammonium, pyridinium, quinolinium, protonated aromatic amines and protonated aliphatic amines, or combinations thereof; X is a Group IIIB, IVB, VB, VIB or transition metal; M is molybdenum or tungsten or combinations thereof; M' is vanadium; M" is independently zinc or a transition metal different from M and M', or combination thereof; z is the charge on said cation C; k is 1 to 5, m is 5 to 18, x is 0 to 6, n is 0 to 3; y is 18 to 62; and when "az" equals "e", there are no protons present in the polyoxometallate support.

The catalysts useful in the process of the present invention may be promoted by various means including preparing the HPA in the presence of vanadyl acetylacetonate or the Like. In addition, exchange of iron or other transition metals, actinide and lanthanide metals, and other groups, G, has been found to promote the activity of the Wells-Dawson HPAs of the catalysts used in the process of the invention.

The invention comprises a process for conversion of alkanes to unsaturated carboxylic acids by contacting an alkane with an oxidizing agent under partial oxidation and dehydrogenation conditions with an HPA supported on a POM salt, thereby to convert said alkane to an unsaturated carboxylic acid or, when ammonia is added to the feed, an unsaturated nitrile. Either or both of the HPA and the POM, independently, may be framework substituted or not as described herein. In one embodiment comprising a substituted POM support, the POM may comprise (1) at least 11 atoms of a first framework metal or metals comprising molybdenum or tungsten, or combinations thereof and (2) at least one atom of a second framework metal or metals comprising zinc or a transition metal other than molybdenum or tungsten. When there is more than one second framework metal, they may comprise a combination of zinc and the available transition metals. Independently of the composition of the POM support, the HPA may comprise 18 atoms or less of molybdenum as framework metal, or may contain a combination (totalling 18 atoms or less) of molybdenum framework atoms and tungsten framework atoms. If the HPA contains fewer than 18 atoms of Mo and/or W, it will also comprise one or more second framework metal or metals, comprising zinc or a transition metal (other than Mo or W) or combination thereof.

In one embodiment, either or both of the HPA and POM support used in the process of the invention may independently comprises 12 to 17 atoms of a first framework metal selected from the group consisting of molybdenum or tungsten, or combinations thereof, and 1 to 6 atoms of a second framework metal such as titanium, zirconium, vanadium, niobium, tantalum, chromium, manganese, rhenium, iron, cobalt, nickel, ruthenium, rhodium, palladium, osmium, iridium, platinum, copper or zinc. The second framework metals (M') may be site-specific, regioselective substitutions or may be essentially randomly substituted in the framework. When the substituted POM support is a Keggin-type POM, it may comprise 9 to 11 atoms of a first framework metal and 1 to 3 atoms of a second framework metal, with the metals as described above.

The central or hetero element, X, of the POM and HPA components of the catalyst useful in the process of the present invention is selected from the elements of Group IIIB, IVB, VB, VIB of the Periodic Table or from the transition elements; it may, for example, be phosphorus, silicon, aluminum, germanium or the like. In these embodiments, the first framework element comprises molybdenum, tungsten, or a combination thereof. An example of such heteropolyacid is $H_6P_2W_{18-n}M'_nO_{62}$, in which phosphorus (P) is the hetero atom and tungsten (W) is the first framework metal and M' is the second framework metal as described below.

The POM or HPA component used in the process of the invention may contain second framework metals which have been substituted into the framework thereof, replacing an equivalent number of the first framework metals. Such substituting metals may, for example, be titanium, zirconium, hafnium, vanadium, niobium, tantalum, chromium, manganese, rhenium iron, cobalt, nickel, ruthenium, rhodium, palladium, osmium, iridium, platinum, copper, zinc or combinations thereof.

The atoms which have been replaced in such substitution may be for example molybdenum or tungsten, or combinations thereof, as disclosed in Ellis and Lyons U.S. Pat. No. 4,898,989, supra; J. P. Ciabrini, et al., *Polyhedron*, 2, 1229 (1983); M. Abbessi et al., *Inorg.Chem.*, 30, 1695 (1991); D. K. Lyons et al., *J.Am.Chem.Soc.*, 113, 7209 (1991). The number of framework atoms replaced may be from 1 to 3 or more, and the substituting metals, which are different from the replaced metal, may each be the same metal, for example iron, or may be different from each other, for example two or three different metal atoms, e.g, one iron atom may replace one tungsten atom; two iron atoms may replace two tungsten atoms, three iron atoms may replace three tungsten atoms; two atoms, different from each other, for example molybdenum and vanadium, may replace two tungsten atoms; three atoms, different from each other, for example manganese, molybdenum and vanadium, may replace three tungsten atoms. In one embodiment, three framework atoms of a POM or HPA are replaced by three atoms, different from the framework atoms, one of which replacing atoms is selected from the group consisting of iron, chromium, manganese or ruthenium, and two of which are different from the one just referred to and are the same or different transition metals.

Examples of such HPAs are $H_7[P_2W_{17}FeO_{61}]$, wherein P is the heteroatom, W is the first framework metal, and Fe is the second framework metal; $H_6[P_2W_{15}Mo_3O_{62}]$, wherein P is the heteroatom, W is the first framework metal, and Mo is the second framework metal; and $H_6[P_2W_{15}Mo_2M'O_{62}]$, wherein P is the heteroatom, W is the first framework metal, and Mo is the second framework metal, and M' is the third framework metal, M' being a transition metal, preferably selected from the group consisting of Fe, Mn, V, Co and Ni. These compositions, as well as their promoted forms, for example with $VO^{2+}$ in the cationic positions, are useful as the HPA component of the supported catalysts.

The supported catalyst comprising a Wells-Dawson-type heteropolyacid (HPA) supported on POM salt may be prepared, for example, by incipient wetness techniques in which a solution of HPA is sprayed on solid support matrix and then dried, or by adding support material to a solution of HPA and evaporating the solution to dryness. The HPA may be dissolved in water or other solvent, such as acetonitrile. The resulting material is then calcined.

The following process illustrates the catalyst preparation using incipient wetness technique. The amounts of POM support and HPA used are determined on the basis of the total pore volume of the support (typically, 0.13–0.18 ml/g) and the desired catalyst loading (typically about 30 wt. %). The desired amount of HPA is dissolved in solvent (typically water or acetonitrile) which may be as much as approximately 25% in excess of the total pore volume of the support material. The solution is sprayed evenly on the support material and the supported catalyst is dried, for example at 100° C. for 1 hour when using water, or 70° C. for 1 hour when using acetonitrile. Repeated spraying and drying steps may be used to modify dispersion characteristics. The final supported catalyst material is then calcined. The calcination temperature is preferably between 250° C. and 450° C., and is not so severe as to damage the catalyst structure. The calcination may be performed, for example, at 275° C. for 3 to 6 hours, or at 420° C. for 1 to 2 hours.

The HPA may usefully be supported on a catalyst support comprising wide pore POM salt. Supported catalysts with HPA loading of approximately 30 weight percent (i.e., 30 wt. % HPA and 70 wt. % support) may be prepared by standard incipient wetness techniques. Modification of this ratio for purposes of manipulating the activity or other characteristics of the catalyst or the process is within the ability of the practitioner of the art. The amount of HPA and POM support used to prepare the supported catalyst may be varied according to the pore volume of the solid support and the degree of catalyst loading desired. These supported catalysts may be prepared, for example, by slurrying the solid support with a solution of the HPA, or by spraying the HPA dissolved in water onto the dried support or by means known in the art. Preferably, the supported catalyst is dried and calcined prior to use.

In one embodiment of the invention, the catalyst is prepared by reacting an HPA with $VO(acac)_2$, isolating the product, and then applying a solution of the product to the support. The supported catalyst is then dried and calcined prior to use.

A variety of in situ techniques can be used to generate a supported Wells-Dawson HPA catalyst, including, for example, precipitating some of the HPA as its cesium salt with cesium carbonate, followed by evaporation to leave the Wells-Dawson HPA on the Cs-POM surface. Another technique is to acidify the surface of a Wells-Dawson POM to generate surface HPA. Regardless of the method used, any Wells-Dawson HPA on a suitable support will be an effective catalyst for converting, for example, propane to acrylic acid. Pure crystalline Wells-Dawson HPAs themselves are active catalysts, but because of their hydrolytic instability and solubility, supported catalysts are preferred.

The catalysts of the present invention have been found to be highly active in the conversion of alkanes to unsaturated carboxylic acids. One important aspect of oxidation catalysts is the redox potential of their active metal sites. Through electrochemical experiments, we have demonstrated that Wells-Dawson HPAs have superior redox properties than Keggin HPAs. FIG. 1 shows the relative reduction potential of Wells-Dawson-type HPAs and Keggin-type HPAs with framework metal substitutions. It can be seen that the Wells-Dawson-type HPA has a wave of more positive reduction potential than the Keggin HPA. In oxidation experiments, we have found that Wells-Dawson HPAs are more efficient catalysts for the oxidation of alkanes to α-β-unsaturated oxidation products than certain Keggin HPAs in comparable experiments. This is consistent with the concept that complexes with more positive reduction potentials leaad to active oxidation catalysts. See also, J. E. Lyons et al., *J.Catal.*, 155, 59 (1995); A. Bottcher et al., *J.Mol.Catal.A*, 113, 191 (1996); T. P. Wijesekera et al., *Catal.Lett.*, 36, 69 (1996).

The data in FIG. 1 show the more positive reduction potential of Wells-Dawson-type Cs-POMs relative to Keggin-type Cs-POMs. Carbon paste electrodes were prepared containing $Cs_xH_{6-x}(P_2Mo_{18}O_{62})$ and $Cs_3(PMo_{12}O_{40})$. As is illustrated in the figure, comparison of the surface electrochemistry of these Cs-POMs showed that the most positive potential of the Wells-Dawson-type ion was over 150 mV more positive than that of the Keggin-type ion.

Figure 2:
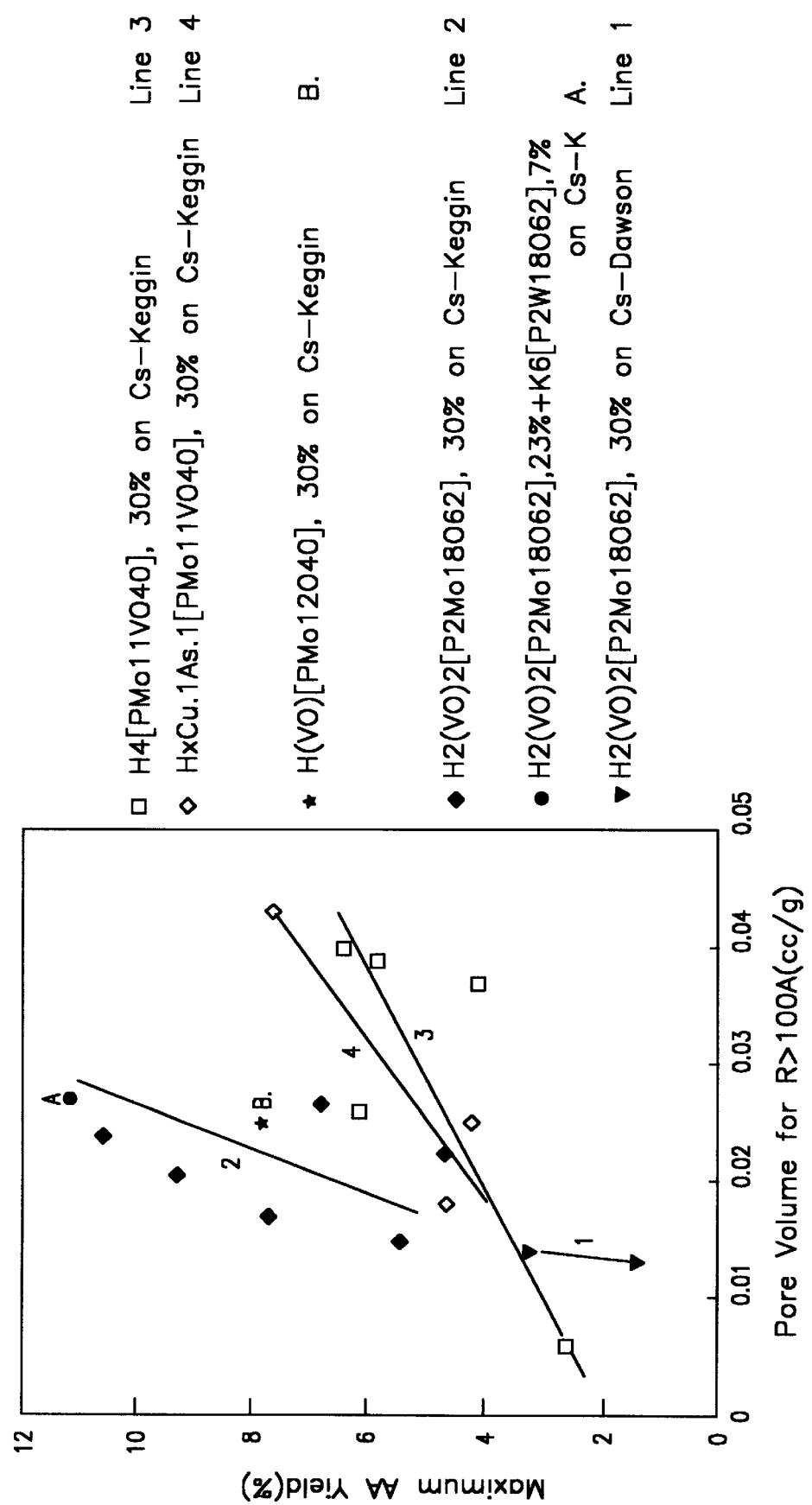
FIG. 2 shows the effect of catalyst support pore volume (in ml/g), for pores with radii greater than 100 Å, on Wells-Dawson-type and Keggin-type catalyst performance as a function of acrylic acid yield.

The data in FIG. 2 shows the effect of catalyst support pore volume (in ml/g), for pores with radii greater than 100 Å, on Wells-Dawson type and Keggin-type catalyst performance as a function of acrylic acid yield. The catalysts, designated in the figure, were prepared as described herein. The figure illustrates that the increase in acrylic acid yield with increasing volume of wide pores is steeper with Wells-Dawson type HPA catalysts than with Keggin-type HPA catalysts. In addition, the figure shows that supported Wells-Dawson type HPA catalysts achieve higher yield values than supported Keggin-type HPA catalysts of the same pore size. This is a comparison of the PSD of the finished catalysts.

EXAMPLES

Example 1

The following procedure for the synthesis of $(NH_4)_6[P_2Mo_{18}O_{62}]$ is an adaptation of that described by Wu (H.Wu, *J.Biol.Chem.*, 189, 43 (1920)). In a 1L rb flask, 100 g $Na_2MoO_4.2H_2O$ was dissolved in 400 ml deionized water; 15 ml phosphoric acid were added, followed by 80 ml concentrated hydrochloric acid. The contents of the flask were refluxed for 8 hours; then cooled to room temperature. One drop of 30% $H_2O_2$ was added and the solution was allowed to stir overnight.

$NH_4Cl$ (100 g) was added to the above solution, stirred for 10 minutes and the yellow product was filtered under suction. The solid was redissolved in a minimum of warm water and refiltered to remove any insoluble material. The filtrate was concentrated in vacuo and diluted with approximately four times its volume of 1,4-dioxane. The solid was washed with dioxane-water (3:1), and diethyl ether and dried in air protected from light. FTIR (v; KBr): 1406, 1077, 1003, 936, 906, 769 $cm^{-1}$. $^{31}P$ NMR (δ; $H_2O/D_2O$): −2.50 ppm (ref: $H_3PO_4$ at 0).

Example 2

The following procedure for the synthesis of $K_6[P_2W_{18}O_{62}]$ is an adaptation of that described in the literature: R. G. Finke, et al., *Inorg. Chem.*, 26, 3886, (1987). In a 1L rb flask, $Na_2WO_4 2H_2O$ (100 g) was dissolved in 350 ml of water, and heated to near reflux. Phosphoric acid (85%; 150 ml) was added dropwise over 30 minutes and continued heating at reflux for 8–12 hours. The reaction mixture was cooled to room temperature, treated with 2 drops of bromine and allowed to stir for 30 minutes. Solid KCl (100 g) was stirred in and $K_6P_2W_{18}O_{62}$ was collected by filtration and dried under suction.

The crude product prepared above was redissolved in approximately 200 ml of hot water and filtered through a celite pad. An equal volume of dioxane was added and the solution was allowed to cool overnight. The product was collected by filtration, washed with dioxane-water (1:4), followed by diethyl ether, and then air dried. The yield was 70–75 g. FTIR (v, KBr): 1090, 1023, 962, 917, 788 $cm^{-1}$. $^{31}P$ NMR (δ; $H_2O/D_2O$): −12.4, −10.8, −11.6 ppm (ref: $H_3PO_4$ at 0).

Example 3

$H_6[P_2Mo_{18}O_{62}]$ was synthesized as follows: A solution of 50 g $(NH_4)_6[P_2Mo_{18}O_{62}]$ dissolved in minimum cold water was passed through 150 g of strongly acidic ion exchange resin (e.g. Dowex HCR-W2, $H^+$ form) packed in an ice-water cooled glass column. The eluate was evaporated to dryness and the residue was further dried on the vacuum-line overnight. FTIR (v; KBr): 1079, 1004, 948, 903, 771 $cm^{-1}$. $^{31}P$ NMR ($\delta$; $H_2O/D_2O$): −2.55 ppm (ref: $H_3PO_4$ at 0).

Example 4

$H_2(VO)_2[P_2Mo_{18}O_{62}]$ was synthesized as follows: A solution of $H_6[P_2Mo_{18}O_{62}]$ (29.84 g) in acetonitrile (325 ml) was treated with a solution of vanadyl acetylacetonate (5.3 g) in acetonitrile (325 ml). The solution was allowed to stir for 1 hour and evaporated to dryness in vacuo. The residual solvent was removed on the vacuum-line overnight and the product was dried in the vacuum-oven at 60° C. for 3 hours and then at 100° C. for 4 hours. FTIR (v; KBr): 1076, 1004, 953, 892, 830 $cm^{-1}$. $^{31}P$ NMR ($\delta$; $H_2O/D_2O$): −4.06 ppm (ref: $H_3PO_4$ at 0).

Example 5

The catalysts $H_2(VO)_2[P_2Mo_{18}O_{62}]$ on $Cs_3PMo_{12}O_{40}$ and $H_6[P_2Mo_{18}O_{62}]$ on $Cs_3PMo_{12}O_{40}$ were synthesized as follows: A solution of the active material $H_6[P_2Mo_{18}O_{62}]$ or $H_2(VO)_2[P_2Mo_{18}O_{62}]$ (quantity required for water was coated on finely ground $Cs_3PMo_{12}O_{40}$ to incipient wetness. The material was dried in an oven at 100° C. for 1 hour, ground again and the procedure repeated until the entire solution was impregnated on the support. The catalyst was finally dried in a vacuum-oven at 100° C. overnight and calcined at 275° C. for 2 hours prior to testing.

Example 6

The catalyst $H_2(VO)_2[P_2Mo_{18}O_{62}]$ on the mixed POM support, $K_6P_2W_{18}O_{62}$ and $Cs_6PMo_{12}O_{40}$, was prepared as follows: Finely powdered $Cs_6PMo_{12}O_{40}$ was slurried in a solution of $K_6P_2W_{18}O_{62}$ in water (10% $K_6P_2W_{18}O_{62}$, 90% $Cs_6PMo_{12}O_{40}$ by allowed to stir for 2 hours. The solvent was evaporated and the residue was dried in a vacuum oven at 120° C. overnight. The mixed POM thus prepared, was used to support $H_2(VO)_2[P_2Mo_{18}O_{62}]$ at a desired level of loading as described in the Example 5 above. The catalyst was dried (100° C. in a vacuum oven overnight), and calcined at 275° C. in air, or at 420° C. under $N_2$, for 2 hours prior to testing.

Example 7

The $H(VO)(PMo_{12}O_{40})$ on $Cs_3(PMo_{12}O_{40})$ catalyst was prepared according to the following process. The amounts of support and heteropolyacid used are determined on the basis of the total pore volume of the support (typically, 0.13–0.18 ml/g) and the desired catalyst loading (typically about 30 wt. %). The desired amount of $Cs_3(PMo_{12}O_{40})$ powder is weighed into a Pyrex dish The total pore volume of the powder is calculated from the BET pore volume. A certain amount of HPA, based on the desired catalyst loading of approximately 30 wt. %, is placed in a beaker and water is added with stirring. After the HPA is dissolved, the solution is sprayed evenly on the support material with a syringe and the supported catalyst is dried at 80° C. for 8 hours. Repeated spraying and drying steps are used to modify dispersion characteristics. The final supported catalyst material is then calcined at 275° C. for 3 to 6 hours.

Likewise, the $H_3(PMo_{12}O_{40})$ on $Cs_3(PMo_{12}O_{40})$ catalyst was prepared according to the following process. $H_3(PMo_{12}O_{40})$ (Fluka) was supported on a wide pore $Cs_3(PMo_{12}O_{40})$ at the 30% level by incipient wetness from an aqueous solution. The catalyst was dried at 100° C. in vacuo overnight followed by heating in air at 275° C. for 2 hours.

Table I shows comparative data for the oxidation of propane catalyzed by Keggin and Wells-Dawson type heteropolyacids supported on Cs-POMs. We have found that the Wells-Dawson-type HPAs produce higher yields of acrylic acid than compositionally comparable Keggin-type HPAs.

TABLE I

Propane Oxidation to Acrylic Acid[a]

| Catalyst | Propane Conv. % | AA Yield % | Selectivity (%)[b] | | | | |
|---|---|---|---|---|---|---|---|
| | | | AA | $C_3^-$ | ACR | Acetic Acid | $CO_x$ |
| $H_3[PMo_{12}O_{40}]$ on $Cs_3PMo_{12}O_{40}$* | 6 | 0.3 | 4.5 | 15.2 | 0 | 10.1 | 69.7 |
| $H_6[P_2Mo_{18}O_{62}]$ on $Cs_3PMo_{12}O_{40}$* | 35 | 4.1 | 11.8 | 2.9 | 0.2 | 17.4 | 67.5 |
| $H(VO)[PMo_{12}O_{40}]$ on $Cs_3PMo_{12}O_{40}$* | 27 | 7.8 | 28.4 | 3.5 | 0.4 | 23.3 | 48.9 |
| $H_2(VO)_2[P_2Mo_{18}O_{62}]^c$ on $Cs_3PMo_{12}O_{40}$** | 33 | 9.2 | 28.4 | 1.6 | 0.2 | 21.5 | 48.1 |

[a]Propane is oxidized in a stream of propane (55 ml/min) and air (28 ml/min) for 24 hours at 350° C. *After this time, the flows are changed to propane (3.2 ml/min), air (16 ml/min) and nitrogen (9.6 ml/min), and propane is oxidized at 370° C. **[After this time, the flows are changed to propane (1.76 ml/min), air (15.8 ml/min) and nitrogen (9.6 ml/min), and propane is oxidized at 375° C.] After a 2 hour equilibration period, gases and liquids are collected and analyzed at 4 hour intervals.
[b]AA = Acrylic Acid; $C_3^-$ = Propylene; ACR = Acrolein; $CO_x$ = $CO_2$ + CO
[c]The molecular formula as determined prior to drying at elevated temperatures, impregnation on the support, and calcination.

What is claimed is:

1. A process for the conversion of alkanes to unsaturated carboxylic acids comprising contacting said alkanes with an oxidizing agent in the presence of a catalyst comprising a heteropolyacid having the formula $H_{(e'-bz')}G_b(X_2M_mM'_xM''_nO_y)^{-e'}$ on a support comprising at least one polyoxometallate having the formula $C_aH_{(e-az)}(X_kM_mM'_xM''_nO_y)^{-e}$, where (a) in the formula of said heteropolyacid, cation G is Cu$^{++}$, Fe$^{+++}$, Co, Mn, Ni, La, Li, Na, K or Rb, or an oxy ion of Ti, V, Cr, Mo, U, As, Bi, Sb, Nb, or ammonium, tetraalkylammonium, pyridinium, quinolinium, protonated aromatic amines or protonated aliphatic amines, or combinations thereof, or is absent; X is a Group IIIB, IVB, VB, VIB or transition metal; M is molybdenum or tungsten, or combinations thereof; M' is vanadium; M" is independently zinc or a transition metal different from M and M', or combination thereof; z' is the charge on said cation G; e' is the charge of anion $(X_2M_{m'}M'_{x'}M''_{n'}O_{y'})$ b is the number of cations G; m' is 12 to 18, x' is 0 to 6, n' is 0 to 3 where m'+x'+n'=18, and y' is 48

(b) in the formula of said support, cation C is selected from the group consisting of potassium, rubidium, cesium, magnesium, calcium, strontium, barium, vanadium, chromium, lanthanum, manganese, iron, cobalt, ruthenium, copper, actinide metal, lanthanide metal, metal oxy anion, ammonium, tetraalkylammonium, pyridinium, quinolinium, protonated aromatic amines and protonated aliphatic amines, or combinations thereof; X is a Group IIIB, IVB, VB, VIB or transition metal; M is molybdenum or tungsten or combinations thereof; M' is vanadium; M" is independently zinc or a transition metal different from M and M', or combination thereof; z is the charge on said cation C; a is the number of cations C; e is the charge of anion $(X_kM_mM'_xM''_nO_y)$; k is 1 to 5, m is 5 to 18, x is 0 to 6, n is 0 to 3 and y is 18 to 62; and (c) said support is a porous material, which material has pore volumes in the range from 0.01 to 0.25 ml/g and a pore size distribution in which more than approximately 60% of said pores have a pore radius of greater than or equal to approximately 75 Å.

2. The process of claim 1 wherein said cation of said heteropolyacid comprises oxy ion of vanadium.

3. The process of claim 1 wherein said heteropolyacid comprises $H_2(VO)_2(P_2Mo_{18}O_{62})$ or $H_6(P_2Mo_{18}O_{62})$ or combination thereof.

4. The process of claim 3 wherein said heteropolyacid comprises $H_2(VO)_2(P_2Mo_{18}O_{62})$ and said support comprises $Cs_3(PMo_{12}O_{40})$.

5. The process of claim 3 wherein said heteropolyacid comprises $H_4(VO)(P_2Mo_{18}O_{62})$ and said support comprises $Cs_3(PMo_{12}O_{40})$.

6. The process of claim 3 wherein said heteropolyacid comprises $H_2(VO)_2(P_2W_{15}Mo_3O_{62})$ and said support comprises $Cs_3(PMo_{12}O_{40})$.

7. The process of claim 3 wherein said heteropolyacid comprises $H_2(VO)_2(P_2W_{15}Mo_2VO_{40})$ and said support comprises $Cs_3(PMo_{12}O_{40})$.

8. The process of claim 3 wherein heteropolyacid comprises $H_2(VO)_2(P_2Mo_{18}O_{62})$ and said support comprises $Cs_6(P_2Mo_{18}O_{62})$.

9. The process of claim 3 wherein said heteropolyacid comprises $H_6(P_2Mo_{18}O_{62})$ and said support comprises $Cs_6(P_2Mo_{18}O_{62})$.

10. The process of claim 1 wherein said cation of said support comprises potassium, rubidium, cesium, magnesium, calcium, strontium, barium, lanthanum, ammonium, tetraalkylammonium, pyridinium, quinolinium, protonated aromatic amines and protonated aliphatic amines, or combinations thereof.

11. The process of claim 1 wherein said support comprises $Cs_6(P_2Mo_{18}O_{62})$.

12. The process of claim 1 wherein said catalyst comprises a heteropolyacid having the formula $H_2(VO)_2(P_2Mo_{18}O_{62})$ and a polyoxometallate support comprising $Cs_3(PMo_{12}O_{40})$ and $K_6(P_2W_{18}O_{62})$.

13. The process of claim 1 wherein said conversion is carried out at a temperature in the range from 225° C. to 450° C.

14. The process of claim 13 wherein said temperature is in the range from 350° C. to 400° C.

15. The process of claim 1 wherein said conversion is carried out in vapor phase.

16. The process of claim 1 wherein said alkanes are selected from the group consisting of alkanes comprising four to seven carbon atoms.

17. The process of claim 16 wherein said alkanes comprise propane or isobutane.

* * * * *